US00PP28898P3

(12) United States Plant Patent
Madsen

(10) Patent No.: US PP28,898 P3
(45) Date of Patent: Jan. 23, 2018

(54) ***CAMPANULA* PLANT NAMED 'PKMP11'**

(50) Latin Name: ***Campanula portenschlagiana* Schult.**
Varietal Denomination: PKMP11

(71) Applicant: Gartneriet PKM A/S, Odense N (DK)

(72) Inventor: Christian Hald Madsen, Korsør (DK)

(73) Assignee: Gartneriet PKM A/S, Odense N (DK)

( * ) Notice: Subject to any disclaimer, the term of this patent is extended or adjusted under 35 U.S.C. 154(b) by 44 days.

(21) Appl. No.: 14/756,952

(22) Filed: Nov. 2, 2015

(65) Prior Publication Data

US 2017/0127599 P1 May 4, 2017

(51) Int. Cl.
*A01H 5/02* (2006.01)

(52) U.S. Cl.
USPC ..... Plt./414

(58) Field of Classification Search
USPC ..... Plt./414
See application file for complete search history.

(56) References Cited

PUBLICATIONS

Printout of application information from PLUTO Plant Variety Database for corresponding Canadian application No. 15-8745 filed Nov. 6, 2015 (1 page) (http://www.wipo.int/pluto).
Printout of application information from PLUTO Plant Variety Database for corresponding CPVO application No. 2015/2111 filed Sep. 11, 2015 (1 page) (http://www.wipo.int/pluto).

*Primary Examiner* — Keith Robinson
(74) *Attorney, Agent, or Firm* — Foley & Lardner LLP

(57) ABSTRACT

A new and distinct cultivar of *Campanula* plant named 'PKMP11', characterized by its compact plant habit; globular plant form; vigorous growth habit; upright dark violet buds and flowers, and small leaves.

3 Drawing Sheets

Figure 1:
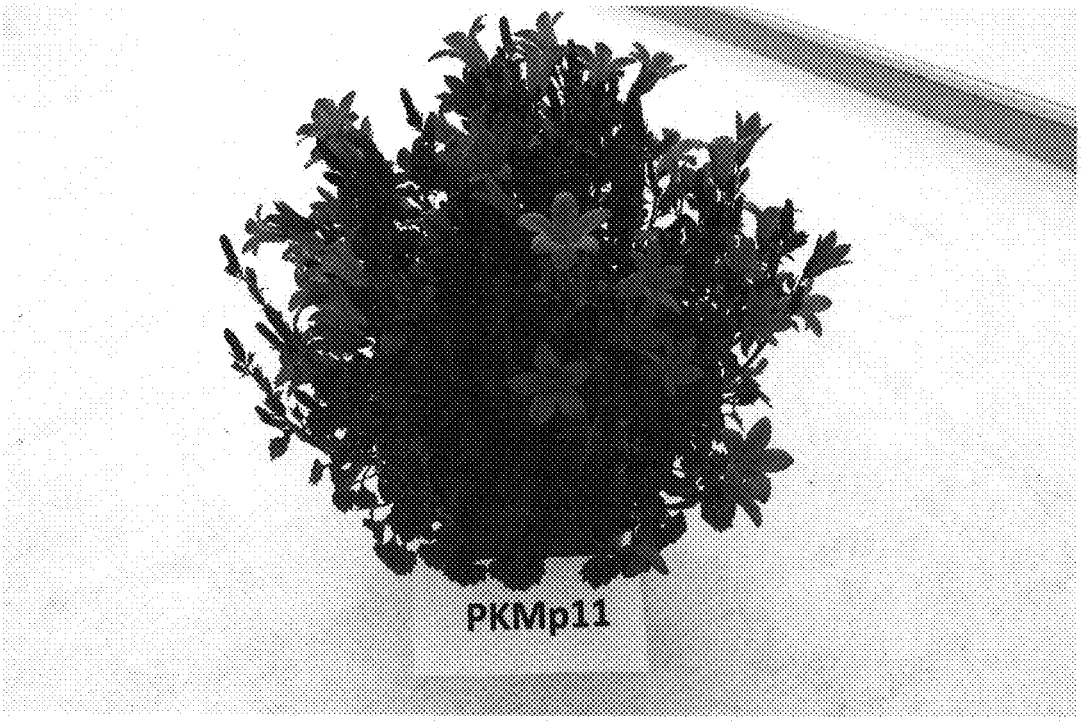

Latin name of genus and species of the plant claimed: *Campanula portenschlagiana* Schult.
Variety denomination: 'PKMP11'.

BACKGROUND OF THE INVENTION

The present invention relates to a new and distinct cultivar of *Campanula* plant, botanically known as *Campanula portenschlagiana* Schult., commonly known as Dalmatian Bellflower, and hereinafter referred to by the name 'PKMP11'.

The new *Campanula*, 'PKMP11', is a product of a planned breeding program conducted by the inventor, Christian Hald Madsen, in Søhus, Denmark. The new *Campanula* originated from a population produced from an open pollinated cross made by the inventor in October 2011 with an unnamed, unpatented, proprietary selection as the female parent and a group of unnamed, unpatented, proprietary selections as possible male parents. The new *Campanula* 'PKMP11' was discovered and selected by the inventor in October 2012 as a single flowering plant within the progeny of the stated population in a controlled environment in Søhus, Denmark. The inventor selected 'PKMP11' on the basis of its compact and freely flowering plant habit and dark purple flowers.

Asexual reproduction of the new *Campanula* cultivar by terminal cuttings has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMP11'. These characteristics in combination distinguish 'PKMP11' as a new and distinct cultivar:

1. Upright plant habit with short upright stems.
2. Bushy globular plant form.
3. Vigorous growth habit, but still needing less chemical growth retardation.
4. Dark violet flowers.
5. No need for vernalization Plants of the cultivar 'PKMP11' can be compared to the *Campanula portenschlagiana* Schult., cultivar 'PKMP05' (patented, U.S. Plant Pat. No. 17,188). In side-by-side comparisons conducted by the inventor in Søhus, Denmark, plants of the instant cultivar 'PKMP11' and plants of the cultivar 'PKMP05' differ in the following characteristics:

1. Plants of 'PKMP11' have darker buds and flowers than plants of 'PKMP05'.
2. Plants of 'PKMP11' have fewer flower buds than 'PKMP05'.
3. Plants of 'PKMP11' have a purple stigma compared to the white of 'PKMP05'

Data on the plants of the parent varieties are no longer available for comparison with plants of the new cultivar *Campanula* 'PKMP11'.

BRIEF DESCRIPTION OF THE PHOTOGRAPHS

The accompanying colored photographs illustrate the overall appearance of the new *Campanula* 'PKMP11', showing the colors as true as it is reasonably possible to obtain in colored reproductions of this type. Colors in the photographs may differ slightly from the color values cited in the detailed botanical description, which more accurately describe the actual colors of 'PKMP11'. Plants in the photographs are shown at 4 months after propagation.

FIG. 1 comprises a side perspective view of a typical flowering plant of PKMP11 grown in a 10.5 cm pot.

Figure 2:
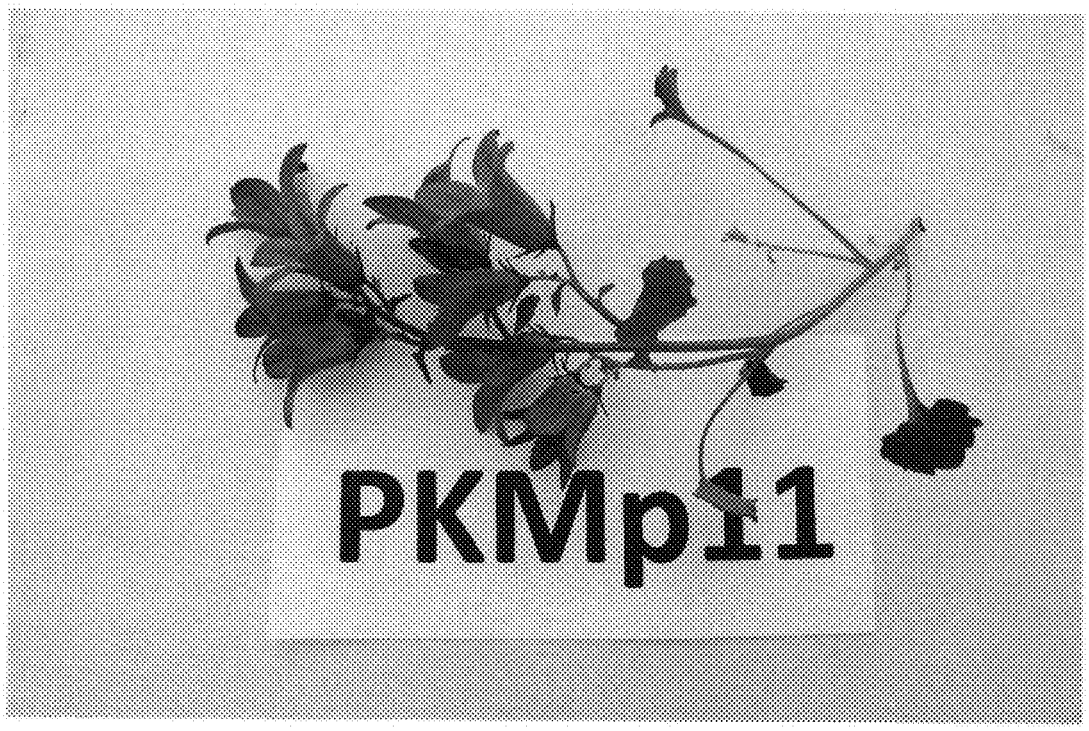

FIG. 2 comprises a close-up view of inflorescence of PKMP11.

Figure 3:
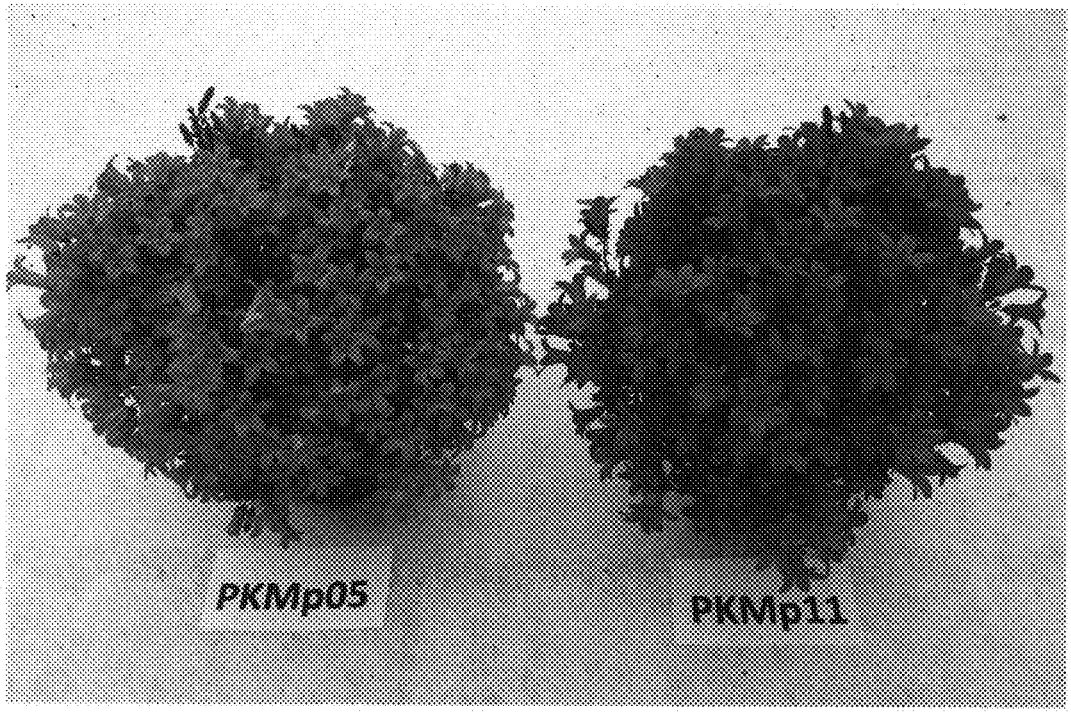

FIG. 3 is a comparison view of a typical flowering plant of PKMP11 with a typical flowering plant of PKMP05.

DETAILED BOTANICAL DESCRIPTION

The new *Campanula* 'PKMP11' has not been observed under all possible environmental conditions. The phenotype of the new cultivar may vary with variations in environment such as temperature, light intensity, day length, and fertility level without any variance in genotype.

The aforementioned photographs, together with the following observations, measurements and values describe plants of the new *Campanula* 'PKMP11' as grown under greenhouse conditions.

The age of the 'PKMP11' plants described is 4 months after propagation. Color references are made to The Royal Horticultural Society Colour Chart (R.H.S.), 5$^{th}$ edition, 2007, except where general colors of ordinary significance are used.

Classification:

*Botanical.*—*Campanula portenschlagiana* Schult.

Parentage:

*Female or seed parent.*—*Campanula portenschlagiana* Schult unnamed, unpatented, proprietary selection.

*Male or pollen parent.*—*Campanula portenschlagiana* Schult unnamed, unpatented, proprietary selection.

Propagation:

*Type cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Perennial, rosette plant with upright plant habit. Campanulate flowers in panicles. Freely branching with lateral branches forming at every node; dense and bushy.

*Crop time.*—After rooting, about 14 weeks are required to produce finished flowering plants in 10.5 cm pots.

*Plant height(from soil level to top of plant plane).*—About 15 cm.

*Vigor.*—Vigorous growth rate.

Lateral branches (stem):

*Number.*—More than 50 per plant; equal to number of inflorescences at base.

*Length.*—Up to 18 cm.

*Diameter.*—3-4 mm.

*Internode length.*—Up to 3 cm.

*Strength.*—Moderate.

*Color.*—RHS 144D.

*Pubescence.*—None.

*Texture.*—Glabrous.

*Lactate.*—Present, small amounts; color RHS 155D.

Foliage description:

*Leaf shape.*—Single, dentate, cordate, palmate venation.

*Leaf length.*—Up to 20 mm.

*Leaf width.*—Up to 28 mm.

*Apex.*—Rounded.

*Base.*—Cordate.

*Margin.*—Broadly dentate, weakly waved.

*Texture (upper and lower surfaces).*—Glabrous, little succulent.

*Color.*—Upper Surface, RHS N137A, Green. Lower Surface, between RHS 137BC (Green) and RHS 191A (greyed green).

*Venation color.*—Lighter green than leaf blade, but areas too small to determine RHS values.

*Venation pattern.*—Reticulate.

*Variegation.*—Absent.

*Number per lateral branch.*—Up to 15.

*Arrangement.*—Alternate.

*Petiole length.*—Up to 6 cm.

*Petiole diameter.*—1-2 mm.

*Petiole color.*—Between 143C and 144B.

Inflorescence description:

*Flower arrangement and shape.*—Single, upright, campanulate flowers in panicles with up to three flowers at lateral branches, flowers with small star shaped calyx.

*Natural flowering season.*—Continuous throughout spring and summer. Season can be extended through long day treatments, no vernalization needed.

*Flower longevity.*—Individual flowers up to three weeks. Flowers persistent.

*Inflorescence size.*—Length: up to 13 cm.

*Buds.*—Length: Approximately 15 mm before opening. Diameter: 2-3 mm. Color: between RHS N87A and RHS N82A, violet. Shape: Ovate to Ellipsoid.

*Flowers.*—Length: About 20 mm. Diameter: About 28 mm. Number per inflorescence: Up to 15.

*Corolla.*—Length of tube: 17 mm. Length of lobe: 10 mm. Width of lobe: 6 mm. Tip of lobe: acute. Curvature: Moderate to strongly reflexing.

*Corolla color.*—Upper and Lower surfaces, between RHS N87A and RHS N82A, violet. Petal Number: 5. Petal Shape: Fused at base to form Corolla. Petal Margin: Entire. Petal Texture: Glabrous (both surfaces). Fragrance: None.

*Petaloid lobes.*—Absent.

*Sepals.*—Arrangement: Free and sessile. Quantity per flower: 5. Length: 5 mm. Width: 2 mm. Overall shape: Triangular. Tip: Acute. Margin: Entire. Color (mature and immature): Upper and lower surfaces: Green and purple, colors mixed and diffuse but purple is more prominent at tip and margins (areas too small to determine R.H.S. values). Texture: Glabrous. Pedicel: Length: up to 20 mm. Diameter: About 1 mm. Color: RHS 144A, yellow-green. Upper part can be purple.

Reproductive organs:

*Gynoecium.*—Pistil and Stigma: Length: Approximately 2 cm. Shape: Conspicuous Tripartite. Color: RHS N85A, violet. Ovary: Color: RHS 144D. Style: Length: Approximately 2 mm shorter than Pistil. Color: RHS N85A, violet and dusted with pollen.

*Androecium.*—Stamen: Number: 5. Anther: Length: 3-4 mm. Diameter: Less than 1 mm. Color: Pale Yellow; dusted with pollen (areas too small to determine R.H.S. value). Pollen: Amount: Moderate to Abundant. Color: Pale yellow (too small to determine R.H.S. value).

Temperature tolerance: 'PKMP11' is considered a winter-hardy perennial in Denmark; not tested with respect to other hardiness zones.

Pest/disease resistance/susceptibility: Not tested.

I claim:

1. A new and distinct cultivar of *Campanula* plant named 'PKMP11', as illustrated and described herein.

* * * * *